US00PP09494P

United States Patent [19]

Zary

[11] Patent Number: Plant 9,494

[45] Date of Patent: Apr. 2, 1996

[54] FLORIBUNDA ROSE PLANT NAMED 'JACSUR'

[75] Inventor: Keith W. Zary, Thousand Oaks, Calif.

[73] Assignee: Bear Creek Gardens, Inc., Medford, Oreg.

[21] Appl. No.: 386,955

[22] Filed: Feb. 10, 1995

[51] Int. Cl.[6] ..... A01H 5/00

[52] U.S. Cl. ..... Plt./25

[58] Field of Search ..... Plt./22, 25, 16, Plt./4

*Primary Examiner*—Howard J. Locker

*Attorney, Agent, or Firm*—Klarquist Sparkman Campbell Leigh & Whinston

[57] ABSTRACT

A floribunda rose plant characterized by the unique combination of its excellent display of well-shaped flowers borne both as single flowers and in clusters, its dark green, glossy, disease-resistant foliage, its vigorous growth and its good plant habit.

1 Drawing Sheet

The present invention relates to a new and distinct variety of rose plant of the floribunda class which was originated by me by crossing the variety JACjem, U.S. Plant Pat. No. 5,001, with the variety JACdew, U.S. Plant Pat. No. 5,122.

The primary objective of this breeding was to produce a new rose variety having the excellent floribunda habit, flower production, disease resistance, and glossy foliage of JACjem combined with the higher petal count, better formed flowers, and very vigorous growth of JACdew. The objective was substantially achieved, along with other desirable improvements, as evidenced by the following unique combination of characteristics that are outstanding in the new variety and that distinguish it from its parents, as well as from all other varieties of which I am aware:

1. Dark green, glossy, disease-resistant foliage;
2. Well-formed flowers;
3. Excellent floribunda habit;
4. Profuse flower production, usually in clusters of 3 to 5; and
5. Vigorous growth.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

Seed parent.—JACjem, U.S. Plant Pat. No. 5,001.

*Pollen parent.*—JACdew, U.S. Plant Pat. No. 5,122.

Classification:

*Botanical.*—*Rosa hybrida.*

*Commercial.*—Floribunda.

FLOWER

Observations made from specimens grown in a garden environment at Somis, Calif. in May through November, 1994.

Blooming habit: Continuous.

Bud:

*Size.*—1¼ inches long when the petals start to unfurl.

*Form.*—The bud form is long, pointed ovoid.

*Color.*—When sepals first divide, bud color is Orange Group 29B. When half blown, the upper and lower sides of the petals are Orange Group 29C.

*Sepals.*—Color: Green Group 139C; often with a reddish color when exposed to direct sunlight. Surface texture: Covered with many fine hairs. There are three lightly to normally appendaged sepals. There are two unappendaged sepals with hairy edges.

*Receptacle.*—Color: Green Group 137D. Shape: Funnel. Size: Small (⅜ inch by ⅜ inch). Surface: Smooth.

*Peduncle.*—Length: Short (1½ inches). Surface: Glandular. Color: Medium green and bronzy when exposed to direct sunlight. Strength: Stiff, erect, and slender.

Bloom:

*Size.*—Medium. Average open size is 3 to 3½ inches.

*Borne.*—Singly and several together in clusters of 3 to 5. If in clusters: Rounded.

*Stems.*—Medium, strong. Average length is about 12 to 14 inches.

*Form.*—When first open: High centered. Permanence: Retains its form to the end, outer petals curl back.

*Petalage.*—Number of petals under normal conditions: 25.

*Color.*—The upper side of the petals is Orange Group 29C. The reverse side of the petals is Orange Group 29C. The base of each petal has a yellow (¼ inch by ¼ inch) half moon at the point of attachment. The major color on the upper side is Orange Group 29C.

*Variegations.*—Occasional whitish green streak down the center of the guard petals (Yellow Group 5C).

*Discoloration.*—The general tonality at the end of the first day: No change. At the end of the third day: No change.

*Fragrance.*—Moderate.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (5 to 6 days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Reddish.

*Stigmas.*—Color: Greenish white.

Form: Bush.

Growth: Vigorous.

Foliage:

*Number of leaflets on normal mid-stem leaves.*— 5.

*Size.*—Medium (5 inches by 4 inches).

*Quantity.*—Abundant.

*Color.*—New foliage: Upper and lower surfaces: Greyed-Orange 173A. Old foliage: Upper surface: Green Group 139A; lower surface: Green Group 139B.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth.

*Stipules.*—Short (½ inch), serrated, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜ inch), hooked downward.

*Color when young.*—Red.

Small prickles:

*Quantity.*—On main stalks: Few. On laterals: Many.

*Color.*—Brown when mature, red when young.

I claim:

1. A new and distinct variety of rose plant of the floribunda class, substantially as herein shown and described, characterized particularly as to novelty by the unique combination of its excellent display of well-shaped flowers borne both as single flowers and in clusters, its dark green, glossy, disease-resistant foliage, its vigorous growth and its good plant habit.

* * * * *

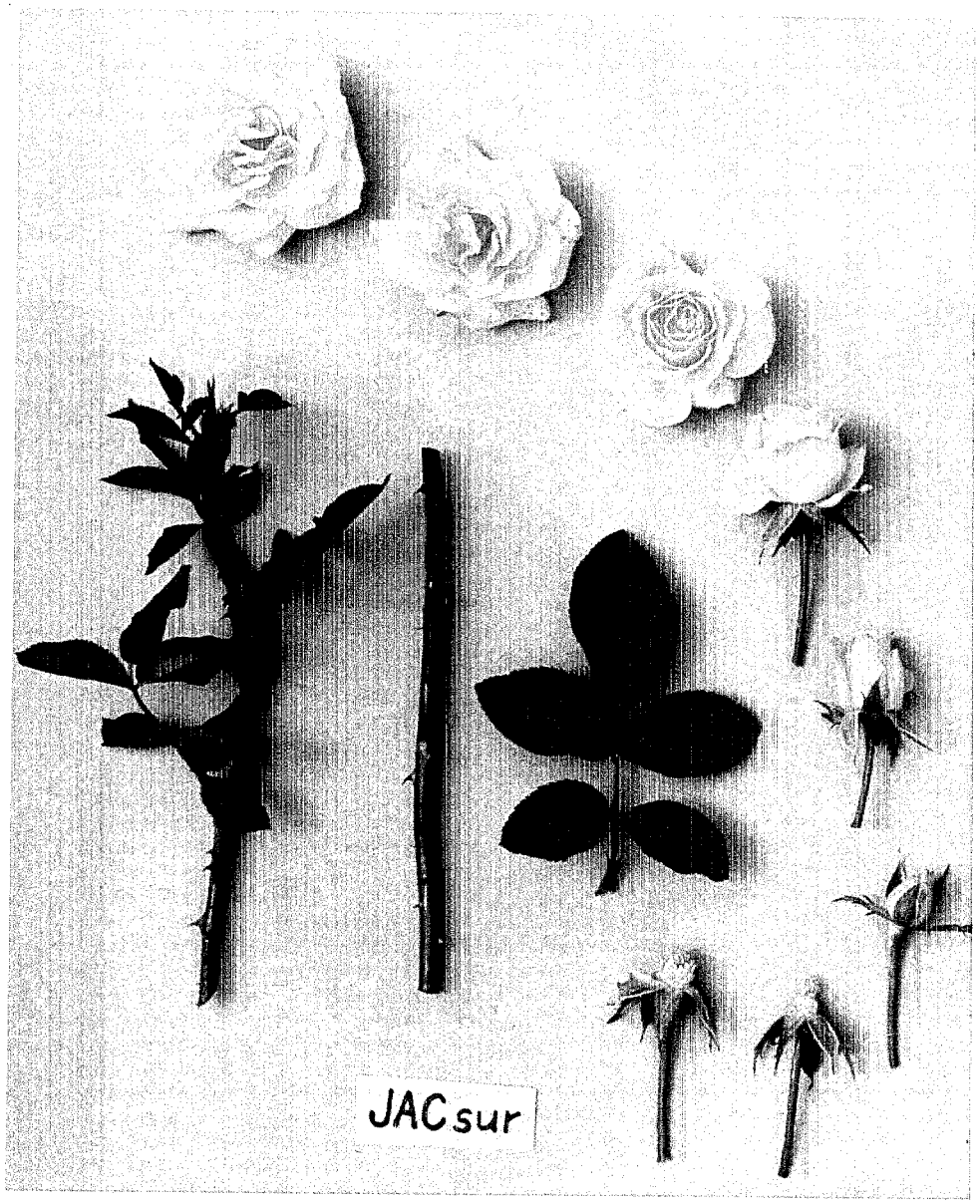
JACsur